(12) United States Patent
Liu et al.

(10) Patent No.: US 12,064,773 B2
(45) Date of Patent: Aug. 20, 2024

(54) METHOD FOR ACCELERATING PARTICLES MATERIAL CLEANING BY STRONG MAGNET AND ITS APPLICATION

(71) Applicant: LVFEN ENVIRONMENTAL PROTECTION TECH. CO., LTD., Beijing (CN)

(72) Inventors: Tianbo Liu, Beijing (CN); Huaiming Peng, Beijing (CN)

(73) Assignee: LVFEN ENVIRONMENTAL PROTECTION TECH. CO., LTD., Beijing (CN)

(*) Notice: Subject to any disclaimer, the term of this patent is extended or adjusted under 35 U.S.C. 154(b) by 0 days.

(21) Appl. No.: 18/027,133

(22) PCT Filed: Nov. 17, 2021

(86) PCT No.: PCT/CN2021/131093
§ 371 (c)(1),
(2) Date: Mar. 20, 2023

(87) PCT Pub. No.: WO2022/105773
PCT Pub. Date: May 27, 2022

(65) Prior Publication Data
US 2023/0330684 A1    Oct. 19, 2023

(30) Foreign Application Priority Data

Nov. 17, 2020   (CN) ......................... 202011282871.9
Nov. 17, 2020   (CN) ......................... 202022651236.5
(Continued)

(51) Int. Cl.
*B03C 1/30*   (2006.01)
*A61L 2/00*   (2006.01)
(Continued)

(52) U.S. Cl.
CPC .............. *B03C 1/30* (2013.01); *A61L 2/0047* (2013.01); *A61L 2/10* (2013.01); *A61L 2/26* (2013.01);
(Continued)

(58) Field of Classification Search
CPC ... B03C 1/30; B03C 2201/20; B03C 2201/22; A61L 2/0047; A61L 2/10; A61L 2/26; A61L 2202/11
(Continued)

(56) References Cited

U.S. PATENT DOCUMENTS 4,631,124 A * 12/1986 Paulson .................... B07B 4/02
209/8
5,035,331 A *  7/1991 Paulson .................... B07B 4/08
209/133
(Continued)

FOREIGN PATENT DOCUMENTS

CN    200963362 Y    10/2007
CN    102319670 A     1/2012
(Continued)

*Primary Examiner* — Terrell H Matthews
(74) *Attorney, Agent, or Firm* — Bayramoglu Law Offices LLC

(57) ABSTRACT

A method and application of accelerating material cleaning with strong magnet particles are provided. The wind airflow enter from the material inlet to accelerate the material, so that the material particles move at a certain speed, and the position and speed of the material can be controlled when it reaches the highest speed; There are internal strong magnetic field units where the material passes, especially when the material reaches the highest speed; Internal strong magnetic field units are used to generate the internal strong magnetic field. According to the method and application, the internal strong magnetic field is used to eliminate the attractive forces such as electromagnetic force, van der (Continued)

Waals force and liquid bridge between the material and the impurities attached to the surface of the material.

20 Claims, 12 Drawing Sheets

(30) Foreign Application Priority Data

Mar. 4, 2021 (CN) .......................... 202110242127.4
Mar. 4, 2021 (CN) .......................... 202120469952.3

(51) Int. Cl.
*A61L 2/10* (2006.01)
*A61L 2/26* (2006.01)

(52) U.S. Cl.
CPC ....... *A61L 2202/11* (2013.01); *B03C 2201/20* (2013.01); *B03C 2201/22* (2013.01)

(58) Field of Classification Search
USPC .......................................................... 209/39
See application file for complete search history.

(56) References Cited

U.S. PATENT DOCUMENTS

| | | | | |
|---|---|---|---|---|
| 5,858,299 A | * | 1/1999 | Fernholz | ............ C11D 17/0073 510/439 |
| 6,595,369 B2 | * | 7/2003 | Paulson | .................. B29C 45/18 209/137 |
| 7,380,670 B2 | * | 6/2008 | Paulson | .................... B07B 7/00 209/133 |
| 7,621,975 B2 | * | 11/2009 | Schneider | ................. B07B 4/02 55/467 |
| 8,783,465 B2 | * | 7/2014 | Ungerechts | ............. B07B 4/025 209/137 |
| 9,302,293 B2 | * | 4/2016 | Schneider | ................. B07B 4/08 |
| 11,762,906 B2 | * | 9/2023 | Madden | .................. G06F 16/53 707/705 |
| 2003/0034277 A1 | * | 2/2003 | Paulson | .................. B29B 13/10 209/31 |
| 2009/0145815 A1 | * | 6/2009 | Schneider | ............... B07B 11/02 209/706 |
| 2023/0330684 A1 | * | 10/2023 | Liu | .......................... A61L 2/10 |

FOREIGN PATENT DOCUMENTS

| | | |
|---|---|---|
| CN | 103639043 A | 3/2014 |
| CN | 104495851 A | 4/2015 |
| CN | 107433055 A | 12/2017 |
| CN | 108325295 A | 7/2018 |
| CN | 108576572 A | 9/2018 |
| CN | 208787089 U | 4/2019 |
| CN | 113145290 A | 7/2021 |

* cited by examiner

Step 1, the first level of accelerated separation
It is the first level of material separation of impurities: the use of strong magnetic field unit and a level of accelerated separation unit to achieve a level of accelerated separation under the action of a strong magnetic field

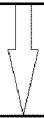

Step 2, the second level of gravitational separation
By using the secondary gravitational force, the separation unit in the strong magnetic field and conductive flanking mechanism to eliminate the gravitational force, the level is the main battlefield to eliminate the gravitational force of the material

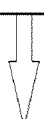

Step 3, three-stage fluidized billowing separation
By using the three-stage fluidized billowing unit, the material will be fluidized and billowed, and the gravitational force will be eliminated once again, and the pure gas will be used to fully wash, separate and purify the material;

Step 4, following the three-stage purification, the impurity content of the material can be up to 15ppm after treatment by the cleaners with optimized parameters.

FIG. 2A

METHOD FOR ACCELERATING PARTICLES MATERIAL CLEANING BY STRONG MAGNET AND ITS APPLICATION

CROSS REFERENCE TO THE RELATED APPLICATIONS

This application is the national phase entry of International Application No. PCT/CN2021/131093, filed on Nov. 17, 2021, which is based upon and claims priority to Chinese Patent Application No. 202022651236.5, filed on Nov. 17, 2020; Chinese Patent Application No. 202011282871.9, filed on Nov. 17, 2020; Chinese Patent Application No. 202110242127.4, filed on Mar. 4, 2021; and Chinese Patent Application No. 202120469952.3, filed on Mar. 4, 2021, the entire contents of which are incorporated herein by reference.

TECHNICAL FIELD

The invention relates to the technical field of material cleaner, in particular to a method of accelerating material cleaning with strong magnet particles and its application, which is specially used for removing impurities in non-metallic materials, thereby improving the quality of materials.

BACKGROUND

In real production and life, some material will produce impurities in some production stages, such as wheat, crumbs in rice, bran and broken case; Powder, ribbon, etc. in plastic; Powder, particles, etc. mixed in tablets and medicine granules are unfavorable to the subsequent production. Therefore, it is an important demand to remove these impurities in order to produce higher quality products.

When the impurities in the material are mixed with the material, according to the present invention, they generally exist in two states, one is dispersed and the other is adhered (attached). Dispersion, that is, impurities and material exist separately, and they can be separated under the blowing of general strength gas during scattering; Adhesion means that impurities and material adhere together under the action of various gravitations, and it is difficult to separate them by scattering. When the downstream process has low requirements for the material, it is enough to separate the dispersed materials. However, with the continuous improvement of the material quality, the requirements for impurity content are getting higher and higher, and only separating the dispersed impurities in the material can no longer meet the requirements. Therefore, it is necessary to separate the impurities in the adhesive materials.

Sometimes, for some reasons, the material may breed some bacteria or microorganisms, which may cause the material to become moldy, deteriorated or even toxic and harmful, thus causing very serious damage to the quality of the material. Therefore, removing these other impurities is also an important demand of production.

In the previous material purification system, the impurity removal efficiency was not high, incomplete and unstable, which also had a great negative impact on the downstream process, fettered the improvement of the production efficiency of the whole production line, and had a high investment cost. This system can effectively make up the shortcomings of the existing similar products, improve the customer's experience and product quality, and make the impurity content of material reduced to 15 ppm after the cleaner with optimized parameters.

SUMMARY

A technical problem to be solved by the present invention is to provide a method of accelerating material cleaning with strong magnet particles and its application. In order to improve the quality of material, remove impurities in material more efficiently and reduce the investment cost.

The invention is realized by the following technical scheme:

The method of accelerating material cleaning with strong magnet particles, which refers to granular materials, is characterized in that, Entering from the material Inlet, wind airflow cooperate with the accelerator to accelerate the material, which makes the material particles move at a certain speed. The position point and speed of the material when it reaches the highest speed can be controlled, that is, the material speed is controlled by the wind speed, and the position point when the material reaches the highest speed is the speed at the end of the accelerator.

A strong magnetic field unit is arranged at any place between the entrance of the material inlet and the exit of the material, especially near the position where the material reaches the highest speed. The internal strong magnetic field is generated by the built-in strong magnetic field unit, and the electromagnetic force generated by running the material at a certain speed to cut the magnetic lines is used to separate or weaken the attractive force such as electromagnetic force between the material and impurities on it;

The internal strong magnetic field can be used to eliminate the attractive forces such as electromagnetic force, van der Waals force and liquid bridge between the material and the impurities attached to the surface of the material. At the same time, it can be used to improve the cleanliness of the material by cooperating with the wind airflow and friction collision with the internal parts to weaken the attractive forces such as van der Waals force and liquid bridge between the material particles and the impurities attached to it.

Furthermore, the material is granular material, and the particle size is 500 µm-20 mm.

Furthermore, the strong magnetic field is generated by strong permanent magnet materials or electromagnetic coils distributed in one or more places, and the magnetic induction intensity distributed near the area where the material flows at a high speed and located at the installation point 2 mm of the strong magnet is better than 600 gauss. The strong magnetic field unit is integrated, attached and matched with other units in physical space, and together with moving particles and impurities, electrostatic and remanence existing between particles and impurities attached to their surfaces can generate electromagnetic force in opposite directions, so that the two units can generate gaps or separate, and the attached impurities can be transformed into dispersed impurities, thus improving the cleaning effect.

Further, the wind airflow includes at least two-stage separation, including one or more permutations and combinations of accelerated separation, gravity removal separation and fluidized billowing separation.

Further, the accelerated separation includes the following steps: the internal strong magnetic field unit and the accelerated separation unit are used to realize the accelerated separation under the action of the internal strong magnetic field, The acceleration of material depends on the airflow ejected by the accelerator in the accelerated separation unit acting on the material particles to accelerate them step by step or single stage, resulting in rapid movement;

At the end of the material accelerated separation unit, the particle speed should be accelerated or adjusted to more than 0.2 m/s. The higher the speed, the better the purification effect, but the higher the speed will damage the particles. Therefore, the particle speed should be set at an upper limit, generally lower than 50 m/s, which depends on the nature of the specific material.

Further, the gravitational separation includes the following processes: when the material still carrying impurities passes through it, the impurities will be taken away by the high-speed airflow here; At the same time, the strong magnetic unit on flank mechanism provides a strong magnetic field here, so it is also the main place to remove electromagnetic force.

Gravity removal separation unit includes conductive and grounded flank mechanism and a strong magnetic field unit arranged on the flank mechanism. Under the action of the built-in strong magnetic field unit and conductive and grounded flank mechanism, the attraction and static electricity on material are eliminated. When the flying material collides with the flank mechanism, the residual impurities attached to the surface of the material will be separated from the material under the collision friction, and this part of the separated impurities will be taken away by the high-speed airflow and flow to the gas outlet.

Further, fluidized billowing separation includes the following processes: fluidization unit is used to fluidize the material, the attraction between granular materials and impurities attached to its surface is eliminated again, and pure gas is used to fully wash, separate and purify the material, so as to enhance the separation effect of the material and impurities.

Furthermore, the fluidized billowing separation is realized by adjusting the size of the fluidization plate hole in the fluidization unit from 0.5 mm to 5 mm and the opening degree of the wind valve.

Furthermore, if the material is wet or absorbs moisture or suffers from other reasons, it may breed some bacteria or mold, resulting in deterioration and failure of the material. One or more of spectrum generator, microwave generator or plasma generator can be used for auxiliary gravitational elimination and sterilization of materials, cleaner internals, gases and impurities. The wavelength of spectrum emitted by spectrum generator is 250~280 nm, and its illumination intensity should be controlled above 18 $\mu W/cm2$.

Furthermore, if the material is wet or absorbs moisture or is subjected to other reasons, it may breed some bacteria or molds, which may lead to deterioration and failure of the material. spectrum generator can be used for auxiliary gravitational elimination and sterilization of materials, cleaner internals, gases and impurities. The wavelength of spectrum emitted by spectrum generator is 250~280 nm, and its illumination intensity should be controlled above 18 $\mu W/cm2$.

The application of method of accelerating material cleaning with strong magnet particles is characterized in that it is applied to material cleaner to obtain a strong magnet particle acceleration material cleaner.

The application of method of accelerating material cleaning with strong magnet particles is characterized in that it is applied to a material purification system to obtain a strong magnet particle accelerating material purification system.

The invention has the following beneficial effects:

1. The invention lies in that the accelerator enables particles to have a certain speed, which can produce two effects:
   1) under the strong magnetic field, the electrostatic particle material and the impurities attached to it are repelled by the electromagnetic force, which is opposite to the original van der Waals force, liquid bridge, electrostatic force and magnetic force, thus reducing the attraction, loosening or separating the adhesion of particles and impurities;
   2) material particles with a certain speed hit the wing plate, so that the impurities attached to it are shaken and separated from the material particles. Strong magnetic field also has the effect of magnetic separation between particles and attached impurities due to different magnetic forces.
2. Another advantage of the invention is that the number and sequence of three different separation methods can be arbitrarily adjusted, and the separation efficiency is much higher than that of the traditional method by matching the wind airflow. The impurity content of the material can be reduced to 15 ppm after parameter optimization.
3. The invention has high impurity removal efficiency, which not only can remove impurities in the conventional sense, but also can remove other kinds of "impurities" such as bacteria and viruses due to the introduction of spectrum generator, and at the same time, it also takes into account gravity-assisted removal, so it is cleaner.
4. When applied to the material cleaner, the invention has the advantages of simple structure, high separation precision, convenient operation, small volume and strong applicability.
5. When the invention is applied to the material purification system, it can be an open-loop system or a closed-loop system; It can also be designed into automatic control or manual control according to different requirements.
6. Compared with the technical progress of the external electromagnetic coil, the invention adopts the built-in strong magnet:
   1) the built-in strong magnet can fully guarantee the magnetic induction intensity in the case, but the external electromagnetic coil can't. Especially, the case of the separation device is usually made of carbon steel or 316 stainless steel, etc. The magnetic field shielding property of these metal materials makes the magnetic field outside the case attenuate completely after it enters the shell.
   2) The built-in strong magnet can fully guarantee the magnetic induction intensity in case, but the external electromagnetic coil can't. When the magnetic induction intensity is inversely proportional to the cubic power of the distance from the magnetic source to the magnetic field point, or the increase of the distance will make the magnetic induction intensity decrease according to the cubic relationship. Even if the external magnetic induction intensity of case is not attenuated by shielding and distance, the external magnetic field will remain weak when it reaches the separation point in vivo.
   3) The built-in strong magnet can fully guarantee the strong magnetic induction intensity in the case, but the external electromagnetic coil can't. The magnetic field generated by the electromagnetic coil is proportional to N*I, and the volume of the coil with larger current I will be larger, and the volume of the coil with larger current I will also be larger. With the same magnetic induction intensity, strong magnet will be smaller.

If the magnetic induction intensity of strong magnet is to be reached, the external electromagnetic coil will be a huge one, which is not comparable with strong magnet.

4) The external electromagnetic coil needs to continuously consume current, which is not energy-saving.

5) External electromagnetic coil will produce harmonic radiation of electromagnetic field, which is electromagnetic pollution.

6) Strong magnet can realize the distributed setting in case, which can achieve the best effect, but the external electromagnetic coil is powerless.

Figure 1A:
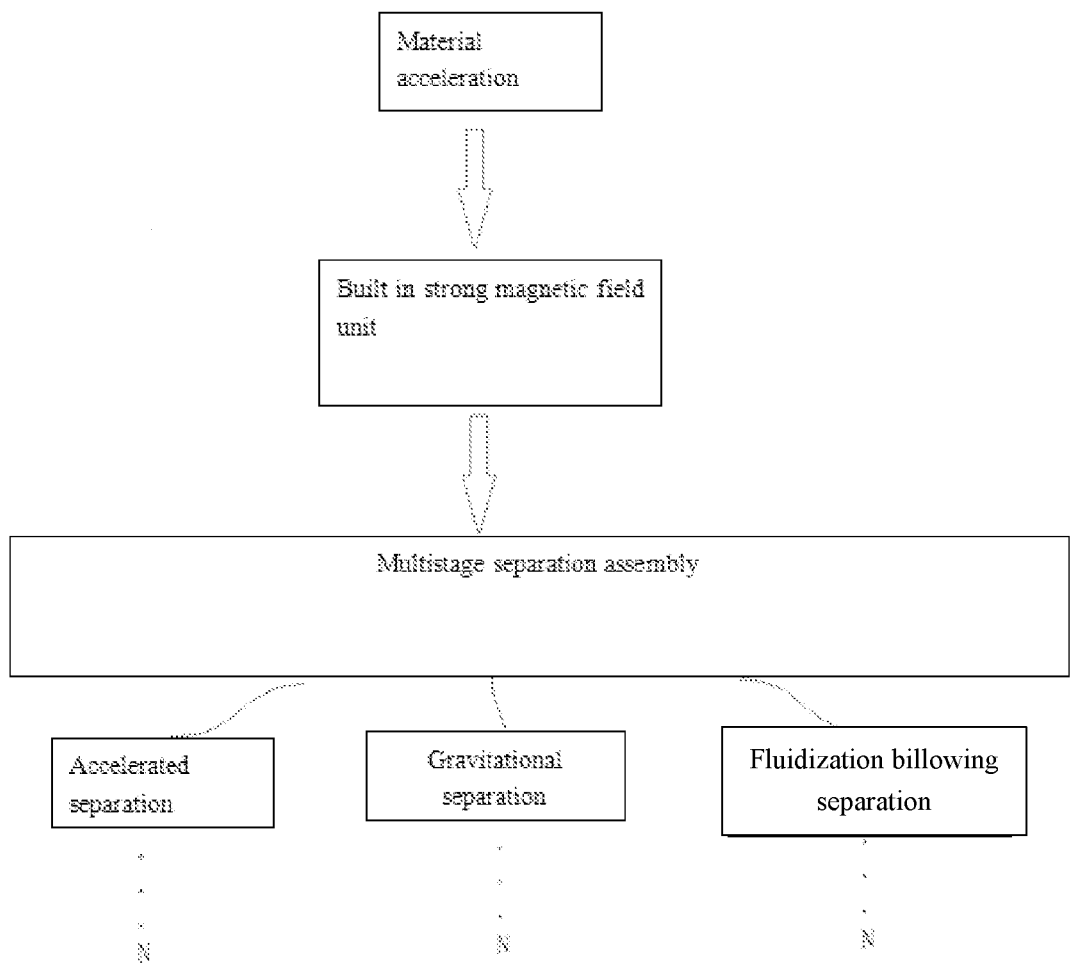
FIG. 1A Block diagram of method of accelerating material cleaning with strong magnet particles FIG. 1B Method of accelerating material cleaning with strong magnet particles application-front view of cleaner FIG. 1C Method of accelerating material cleaning with strong magnet particles application-side view of cleaner FIG. 1D Front view of method of accelerating material cleaning with strong magnet particles application-accelerated separation unit FIG. 1E Side view of application of method of accelerating material cleaning with strong magnet particles-accelerated separation unit FIG. 1F Detailed diagram of application of method of accelerating material cleaning with strong magnet particles-accelerated separation unit FIG. 1G Flow chart of method of accelerating material cleaning with strong magnet particles FIG. 1H Method of accelerating material cleaning with strong magnet particles-details of application of fluidization board FIG. 1I Application of method of accelerating material cleaning with strong magnet particles-axonometric FIG. 1A FIG. 1J Application of method of accelerating material cleaning with strong magnet particles FIG. 2A FIG. 1K Schematic diagram of a part of strong magnet (coil) installation position of method of accelerating material cleaning with strong magnet particles FIG. 1L Schematic diagram of a spectrum generator installation site applied by the method of accelerating material cleaning with strong magnet particles FIG. 1M Schematic diagram of application of one-side blanking by method of accelerating material cleaning with strong magnet particles FIG. 2B Method of accelerating material cleaning with strong magnet particles applies two open-loop system FIG. 2C Method of accelerating material cleaning with strong magnet particles applies two closed-loop system FIG. 2A. The flowchart of method of accelerating material cleaning with strong magnet particles in embodiment 1

Wherein each reference numeral is:

material inlet, 2. Material inlet distribution unit, 3. flank mechanism, 4. fluidized billowing separation unit, 5. outrigger, 6. case, 7. accelerated separation unit, 8. internal strong magnetic field Unit, 9. spectrum generator, 10. material exit, 11. gas outlet, 12. gas inlet, 13. clear window, 14. feed bin, 15. valve, 16. cleaner, 17. receiving device, 18. silencer, 19. filter, 20. fan, 21. separator, 22. precision filter, 23 material level controller.

DETAILED DESCRIPTION OF THE EMBODIMENTS

It is believed that it will be clear to those skilled in the art to further explain the technical scheme of the present invention with reference to the following drawings and examples.

As we all know, the Lorentz force will be generated when the electric charge moves in the magnetic field, and the faster the electric charge moves, the stronger the Lorentz force will be. When the material and fine impurities adsorbed together by electromagnetic force flow through the magnetic field, the polarity of the electric charge carried by the material and the impurities is opposite, so the Lorentz force exerted by the material and the impurities is also opposite, and the distance between the material and the impurities will increase, thus weakening and removing the carried electromagnetic force, and at the same time, pulling force will be generated between the particles and the attached impurities.

In the present invention, a technical idea of using strong magnetic field with wind current to realize material cleaning is put forward. The strong magnetic field generated by strong permanent magnet (NdFeB, samarium cobalt, etc.) or the strong magnetic field generated by electromagnetic coil is used to eliminate the attraction between particles and impurities. As for which form to adopt in practical application, it can be determined according to specific conditions, and strong magnet will be more appropriate. Magnetic field intensity should be higher than 600 gauss at 2 mm from the magnet.

The invention has a wide range of applications, and the material selection of case and internal parts is determined according to the characteristics of materials. For chemical products and medical products with high requirements, stainless steel can be used as case and internal parts; for some mineral products, ordinary carbon steel can be used as case or internal parts; for the requirements of grain, feed and other industries, suitable metal materials and even FRP can be used as case and internal parts. Besides welding, the processing technology can also adopt bonding, riveting, linking and other ways.

Example 1

In this embodiment, a method of accelerating material cleaning with strong magnet particles, as shown in FIG. 1A, Entering from the material Inlet, wind airflow cooperate with the accelerator to accelerate the material, which makes the material particles move at a certain speed. The position point and speed of the material when it reaches the highest speed can be controlled, that is, the material speed is controlled by the wind speed, and the position point when the material reaches the highest speed is the speed at the end of the accelerator.

Entering from the material inlet to the material exit, respectively, through at least two stages of separation, including one or more permutation combinations of accelerated separation, gravitational separation and fluidized billowing separation. Using the built-in strong magnetic field to eliminate the attractive forces such as electromagnetic force, van der Waals force and liquid bridge between the materials with static electricity and remanence and the impurities attached to the surface of the materials, and at the same time, improve the cleanliness of the materials with wind airflow.

There is a built-in strong magnetic field unit at any place between the entrance of the material inlet and the exit of the material, especially near the position where the material reaches the highest speed, and the built-in strong magnetic field unit is used to generate an internal strong magnetic field;

The internal strong magnetic field can be used to eliminate the attractive forces such as electromagnetic force, van der Waals force and liquid bridge between the material and the impurities attached to the material surface. At the same time, it can be matched with the wind airflow and the friction collision with the internal parts to weaken the attractive forces such as van der Waals force and liquid bridge between the material particles and the impurities attached to it, so as to improve the cleanliness of the material.

Strong magnetic field is produced by strong permanent magnet materials or electromagnetic coils which are distributed in one or more places. The magnetic induction intensity which is distributed near the area where the material flows at a high speed and located at the installation point of strong magnet 2 mm is higher than 600 Gauss as far as possible. The strong magnetic field unit is integrated, attached and matched with other units in physical space, and together with moving particles and impurities, electrostatic and remanence existing between particles and impurities attached to their surfaces can generate electromagnetic force in opposite directions, so that the two units can generate gaps or separate, and the attached impurities can be transformed into dispersed impurities, thus improving the cleaning effect.

In this embodiment, the first method of accelerating material cleaning with strong magnet particles is listed, as a basic example, as shown in FIG. 2A, which specifically includes the following steps:

Step 1, the first-stage accelerated separation includes the following steps: the internal strong magnetic field unit and the accelerated separation unit are used to realize the accelerated separation under the action of the internal strong magnetic field, The acceleration of material depends on the airflow ejected by the accelerator in the accelerated separation unit acting on the material particles to accelerate them step by step or single stage, resulting in rapid movement;

At the end of the material accelerated separation unit, the particle speed should be accelerated or adjusted to more than 0.2 m/s. The higher the speed, the better the purification effect, but the higher the speed will damage the particles. Therefore, the particle speed should be set at an upper limit, generally lower than 50 m/s, which depends on the nature of the specific material.

It can eliminate the electromagnetic force between the material with static electricity and remanence moving rapidly under the strong magnetic field and the impurities attached to its surface, and at the same time, the scattered impurities in the material that do not adhere to the material are preliminarily removed by wind force.

The unit integrates multiple functions, and it not only provides a wind distribution port, but also makes the air flow jetted by the accelerator above the first-stage accelerated separation unit act on the material, accelerating the movement speed of the material particles step by step or single-stage, at the same time, making the dispersed impurities separate from the material flow. The sliding plate cooperates with the accelerator to increase the collision effect during the operation of the material, so as to eliminate Van der Waals and liquid bridge between the material particles and their attached impurities. The conductivity and sufficient grounding of the sliding plate will discharge the static electricity of the material.

Second, two-stage gravitational separation is the main step of separating impurities from material, which includes the following processes: when the material which is separated from the first-stage acceleration and still carries impurities passes through it, the impurities will be taken away by the high-speed airflow here; At the same time, the strong magnetic unit on flank mechanism provides a strong magnetic field here, so it is also the main place to remove electromagnetic force. Or a region formed by combining a strong magnetic unit on a first-stage accelerated separation unit; When the flying material collides with the flank mechanism, the residual impurities attached to the surface of the material will be separated from the material under the collision friction, and this part of the separated impurities will be taken away by the high-speed airflow and flow to the gas outlet;

Gravity removal separation unit includes conductive and grounded flank mechanism and a strong magnetic field unit arranged on the flank mechanism. Under the action of the built-in strong magnetic field unit and conductive and grounded flank mechanism, the attraction and static electricity on material are eliminated. When the flying material collides with the flank mechanism, the residual impurities attached to the surface of the material will be separated from the material under the collision friction, and this part of the separated impurities will be taken away by the high-speed airflow and flow to the gas outlet.

In gravity removal separation unit, the repulsive force of strong magnet magnetic field is the largest when the material speed is the largest, and the repulsive electromagnetic force between particles and impurities blows away by wind.

Gravitational separation, the wing plate located between the upper and lower cavities of the equipment and its vicinity, is the main step of separating impurities from materials. This stage is the main battlefield for eliminating the gravitational force between materials and the impurities attached to its surface, and the scattered impurities left over from the previous stage are purified by strong air flow again, and the impurities of this stage that have eliminated the gravitational force are simultaneously purified by strong air flow.

Step 3, three-stage fluidize billowing separation: fluidize billowing separation includes that following process: fluidizing and billowing the material by using the fluidization unit, once again eliminating the attraction between the granular material and the impurities attached to its surface, fully washing, separating and purifying the material with pure gas, and enhancing the separation effect of the material and impurities.

The fluidized billowing separation effect can be achieved by adjusting the size of the fluidization plate hole in the fluidization unit to 0.5 mm-5 mm and the opening of the wind valve. After the material is removed and separated by secondary gravity, the clean air blown out from the air outlet under the fluidization plate blows it up, resulting in a "billowing" effect. The clean air fully contacts and acts with the material, causing the material to turn over and collide, thus realizing the full washing of the material. The upper part of the component receives the material from gravity removal separation unit, and the lower part is connected with the clean material outlet; One function of this part of fluidization plate is to take away the residual impurities on the surface of the material, and the other function is to create gas supply conditions for the formation of the upper gravity removal separation unit.

Fourthly, after three-stage purification, the impurity content of the material can reach 15 ppm after being treated by cleaner with optimized parameters.

Example 2

On the basis of the first embodiment, the order and number of separation unit can be adjusted, including one or more permutation combinations of accelerated separation, gravitational separation and fluidized billowing separation.

For example, adjust the order of separation units, such as gravity removal separation unit, accelerated separation and fluidized billowing separation. For example, the first-stage fluidized billowing separation, the second-stage accelerated separation and the first-stage gravity removal separation unit; And so on and so forth.

For example, adjust the number of separation unit, such as one-stage accelerated separation, two-stage accelerated separation, three-stage gravity separation and four-stage fluidized billowing separation; For example, one-stage accelerated separation, two-stage gravity separation, three-stage gravity separation and four-stage fluidized billowing separation. And so on and so forth.

For example, adjust the order and number of separation unit at the same time, such as first-stage accelerated separation, second-stage accelerated separation and third-stage accelerated separation; For example, one-stage accelerated separation, two-stage gravity removal separation unit, and three-stage gravity removal separation unit; And so on and so forth.

Finally, for example, when two-sided blanking components are used, the matching scheme for one-sided blanking can be superimposed.

Example 3

On the basis of the first or second implementation, a further step can be added. If the material is wet or absorbs moisture or suffers from other reasons, it may breed some bacteria or mold, resulting in deterioration and failure of the material. spectrum generator can be used for auxiliary gravitational elimination and sterilization of materials, cleaner internals, gases and impurities. The wavelength of spectrum emitted by spectrum generator is 250~280 nm, and its illumination intensity should be controlled above 18 µW/cm2.

Example 4

The application of method of accelerating material cleaning with strong magnet particles is applied to material cleaner to obtain a strong magnet particle acceleration material cleaner. When cleaner works, the material enters from the material inlet, and the material outlet can be directly connected to the material receiving facilities or equipment, such as: the material packaging machine or bulk tank car, the gas inlet is connected to the air inlet pipeline, and the gas outlet is connected to the gas outlet pipeline; The material inlet enters the equipment, passes through the inlet distribution unit, each separation unit and strong magnetic field unit, and then is discharged from the material exit. The wind force configured in the process acts on the separation units at all levels, and the separated impurities are carried by the gas from the gas outlet and separated from the cleaner, and then enter the supporting gas purification facilities for separation and collection. The above-mentioned separation unit includes one or more permutations of accelerated separation, gravitational separation and fluidized billowing separation.

In this embodiment, the first strong magnet particle acceleration material cleaner is listed as a basic example, as shown in FIGS. 1B to 1M.

Includes a Material inlet distribution unit, a primary accelerated separation unit, a secondary gravity removal separation unit, a tertiary fluidized billowing separation unit, Components such as strong magnetic field unit, case, spectrum generator, material inlet, material inlet, gas inlet, gas outlet, outrigger, clear window, etc. The material moves and flows in a variety of ways in the cleaner according to the set way, and the impurities in the material are separated and separated from the material by various wind forces, thus achieving the function of purifying the material. The treatment capacity is from 100 kg/h to 100 T/h, and the separation accuracy can reach 15 ppm.

The internal structure of the cleaner, in this embodiment, takes rectangular shape and internal two-sided blanking as an example, and includes two groups of blanking components, each group of blanking components includes a Material inlet distribution unit, an accelerated separation unit, The functions of two-stage gravity removal separation unit, three-stage fluidized bed billowing separation unit, strong magnetic field unit, spectrum generator, etc., as mentioned above, will not be described in detail. Their structures are simple, and they are briefly described in detail as shown in the FIG. According to the different properties of materials to be treated, different case and internal materials can be used, such as stainless steel (304, 304L, 316, 316L), common carbon steel, aluminum, plastic resin and glass fiber reinforced plastic.

According to the invention, a strong magnetic field unit is arranged, and by utilizing a strong magnetic field generated by a strong permanent magnet (neodymium iron boron, samarium cobalt), the accelerated material particles can eliminate the electromagnetic force attraction between the impurities and the materials, so as to achieve the purpose of eliminating the electromagnetic force between the impurities and the materials. As far as possible, the permanent magnets of the strong magnet unit are distributed near the area where the material flows at a high speed, and the magnetic field intensity at 2 mm from the installation point should be higher than 600 gauss.

In addition to using strong permanent magnets, this product can also use electromagnetic coil to generate strong magnetic field, so as to eliminate the electromagnetic force between the material and its adsorbed impurities, and connect DC, AC and various harmonic power supplies to the electromagnetic coil. However, the non-DC power supply will generate large electromagnetic radiation, so the radiation intensity should be controlled within the local relevant standards.

In addition, in order to thoroughly eliminate the electromagnetic force between the material and its attached impurities, the strong magnet can be set at many points in the area where the material flows, such as the material inlet of the equipment, the material exit of the equipment, the first-class accelerated separation unit, Secondary gravity ⑤removal separation unit and tertiary fluidized billowing separation unit.

The First Blanking Station, Material Inlet Distribution Unit

The Material inlet distribution unit of the invention is connected with the material inlet, and is provided with an adjustable adjusting plate, and a gap is arranged between the adjusting plate and the upper surface of the first-stage acceleration unit, so that the material can flow out uniformly; The adjusting plate is manually or automatically adjusted by the adjusting mechanism, aiming at uniformly and controllably distributing the materials from the material inlet to the upper surface of the first-level accelerated separation unit;

According to the Material inlet distribution unit, the materials entering the equipment can be uniformly distributed on the sliding plate of the first-level accelerated separation unit, and if the materials are not uniform, the separation effect will be reduced. Different materials may have different fluidity, and materials with good fluidity can flow out evenly from the gap between the regulating plate of the inlet distribution unit and the upper surface of the first-stage acceleration unit; However, the material with poor fluidity may fill the gap between the inlet distribution unit and the lower acceleration unit after entering the equipment from the inlet, so that the material cannot flow out of the gap evenly. Therefore, it is necessary to regulate the regulating plate and its mechanism, so that the material can flow out evenly from the gap between the inlet distribution unit and the upper surface of the first acceleration unit, thus laying the foundation for effective separation of materials and impurities.
Second Blanking Station, First-Stage Accelerated Separation Unit First of all, referring to FIG. 1B, we can see that the area occupied by the first-stage accelerated separation unit just provides an air inlet for the upper space, and this part of air is used to power the accelerated movement of the material.

Figure 1B:
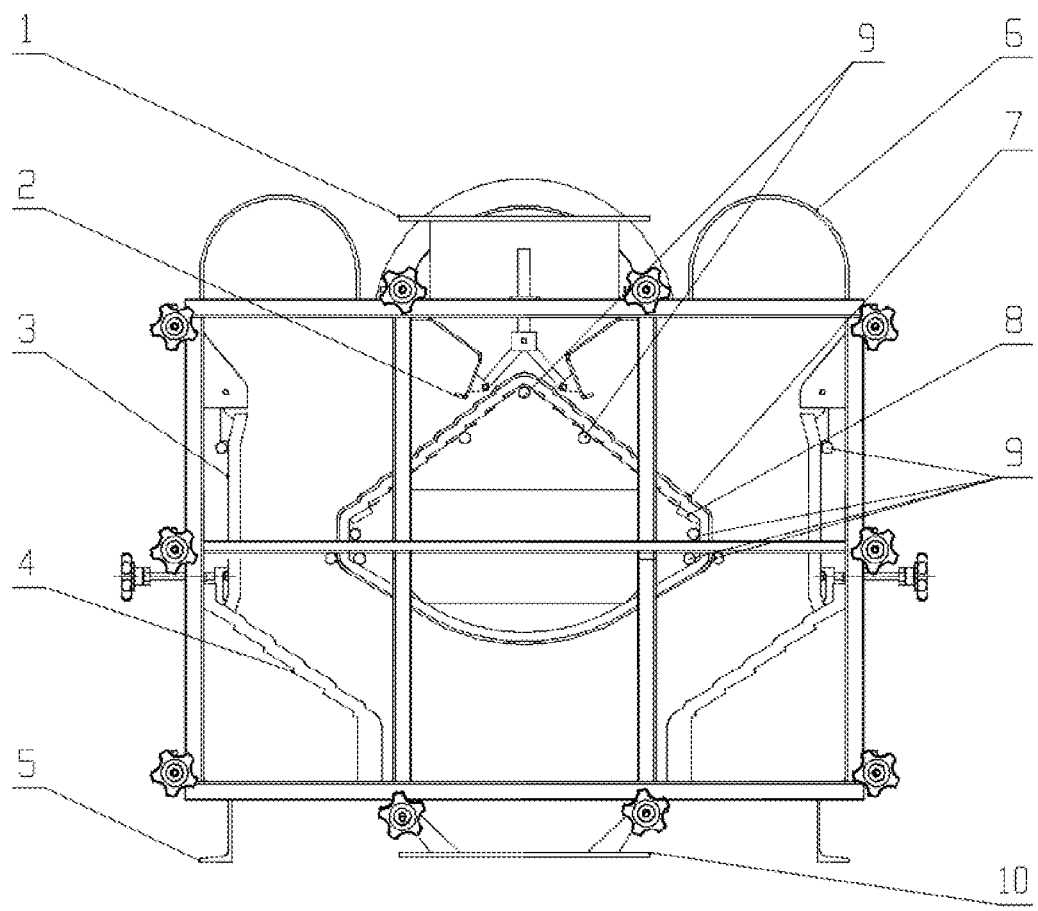
Figure 1C:
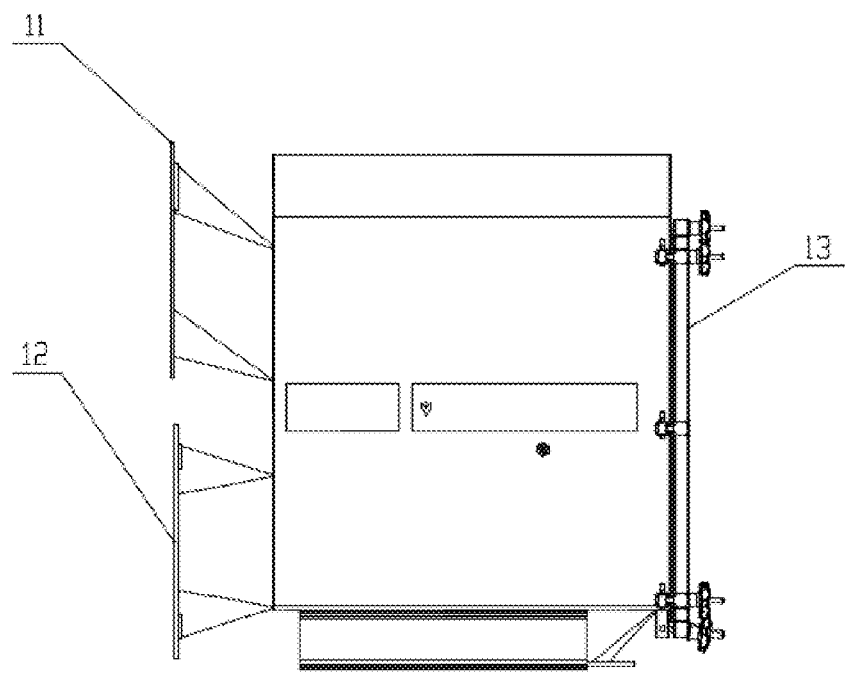
Figure 1D:
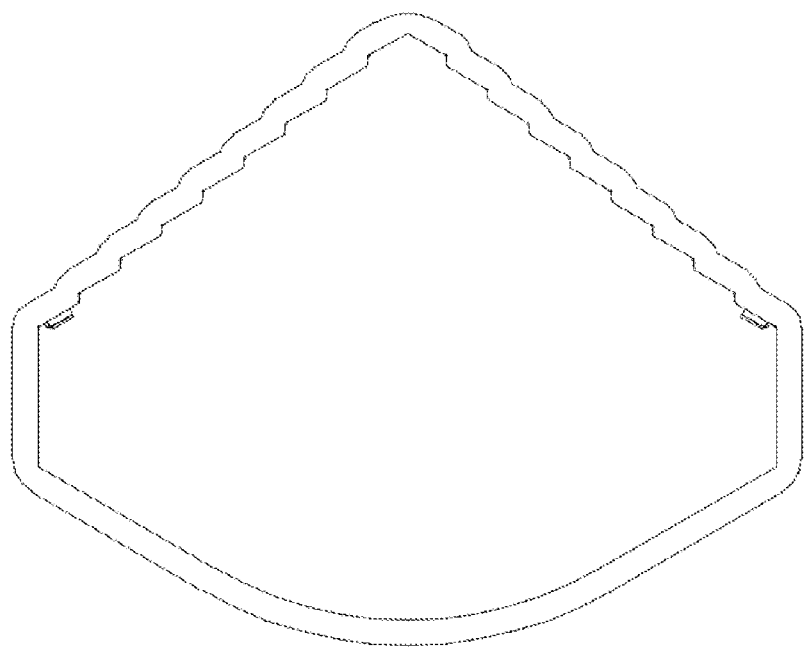
Figure 1E:
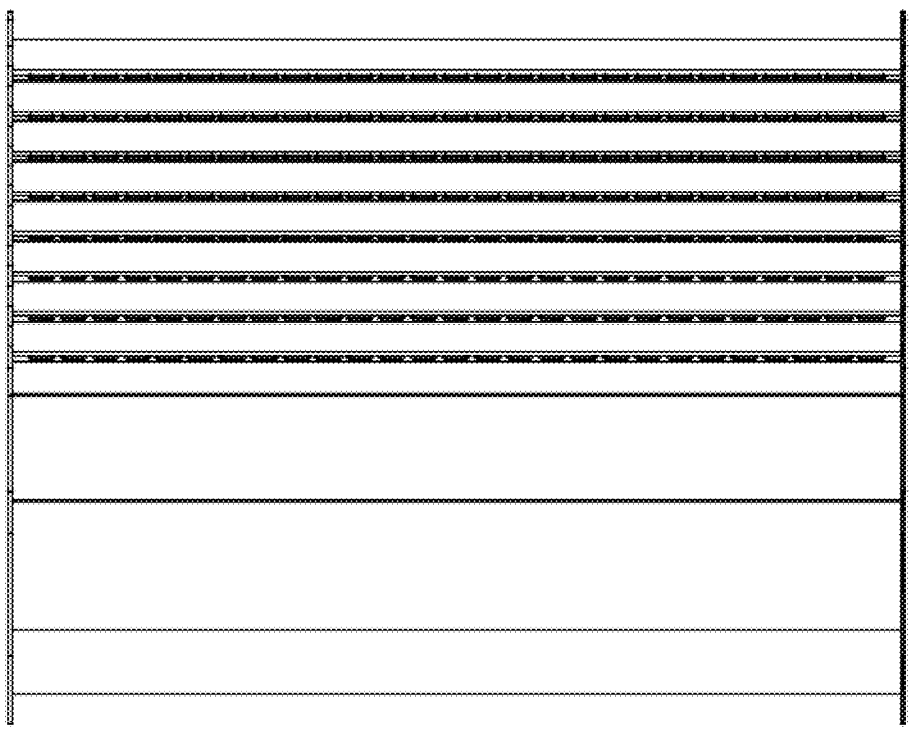
Figure 1F:
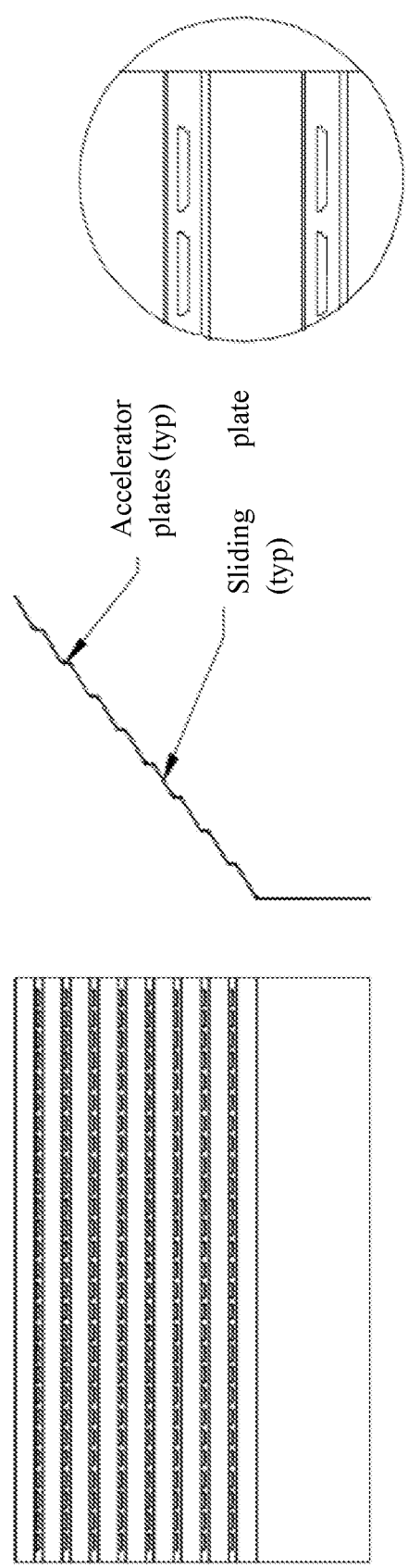
Figure 1G:
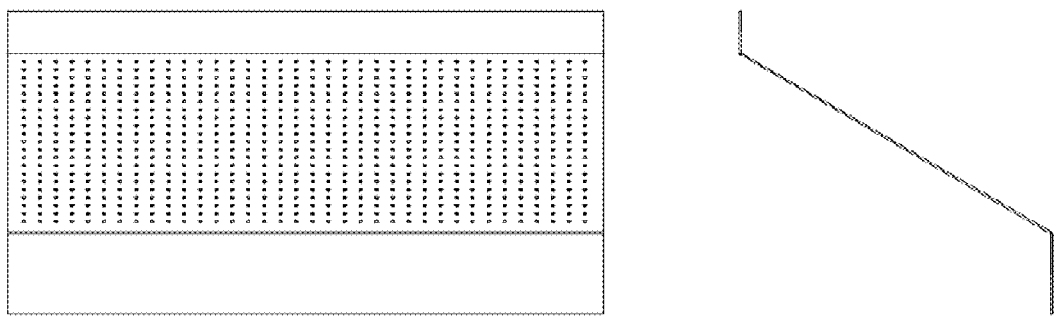
Figure 1H:
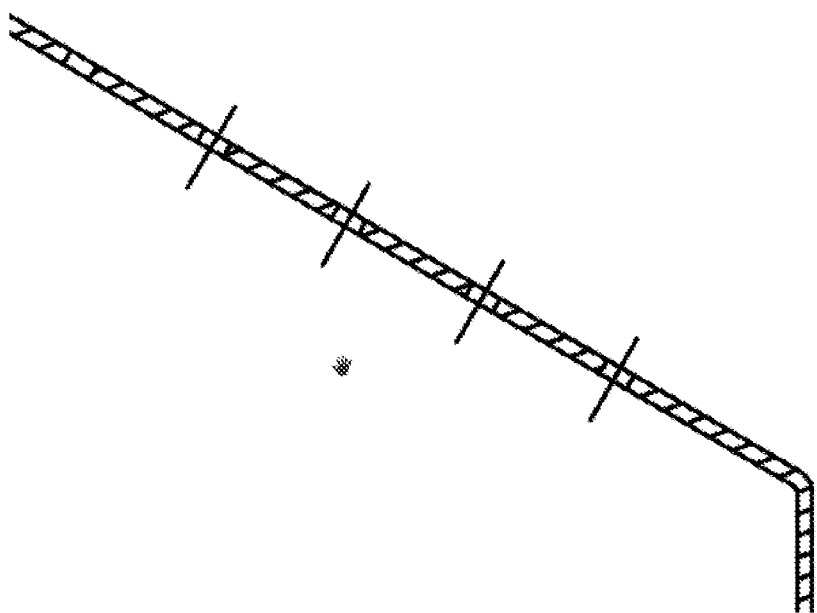
Figure 1I:
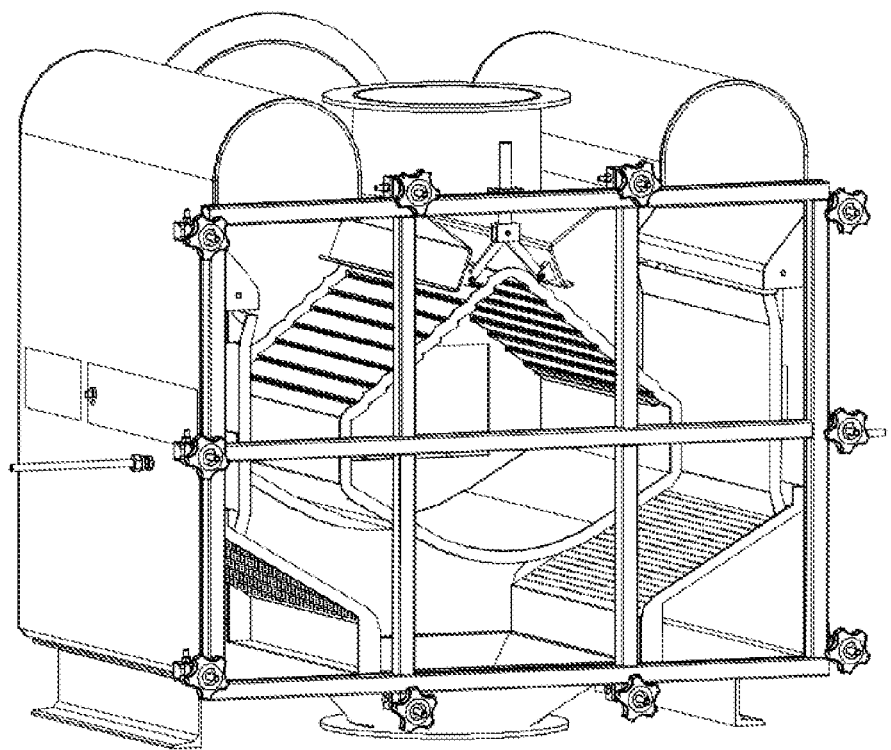
Figure 1J:
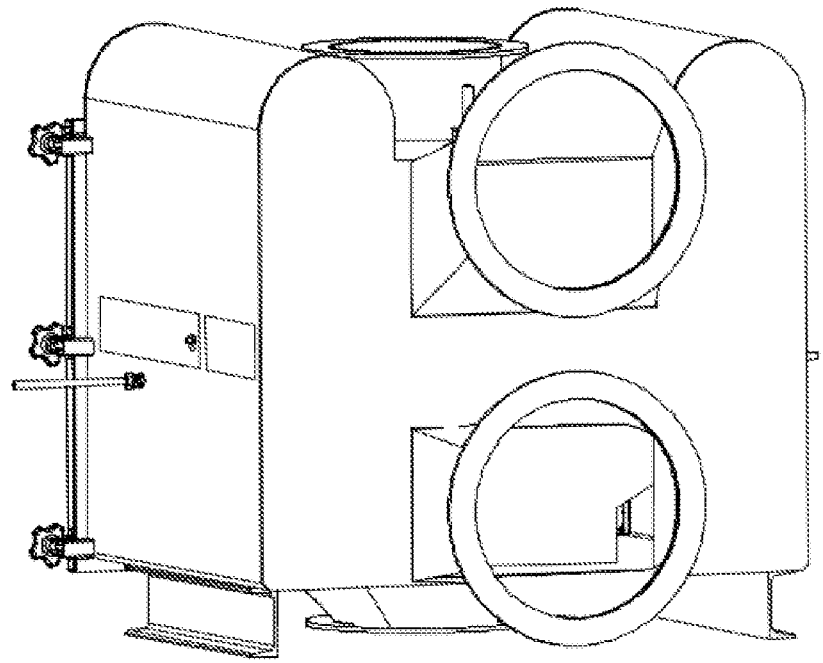
Figure 1K:
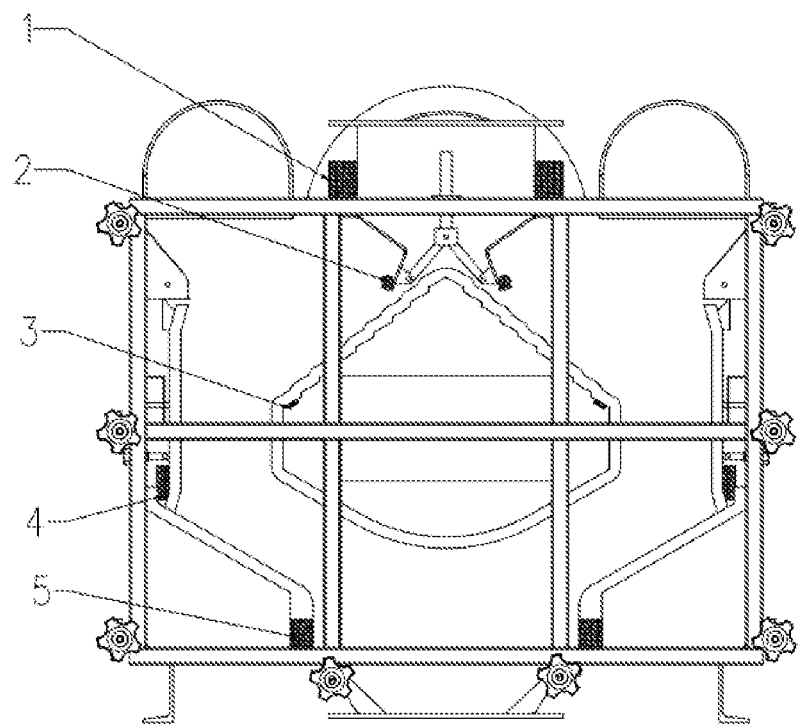
Figure 1L:
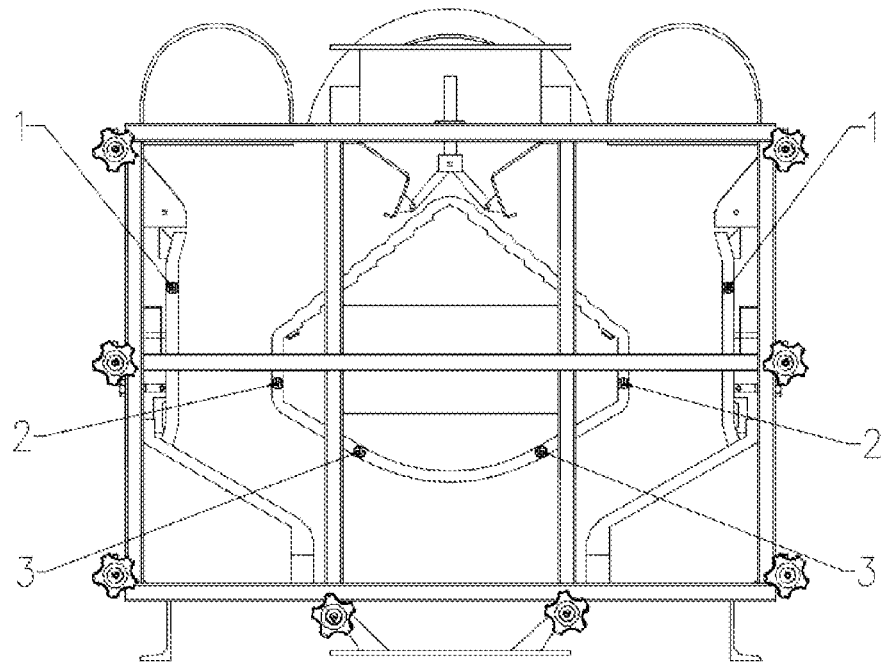

Secondly, referring to FIG. 1F, we can see that the upper surface of the first-level accelerated separation unit is provided with an accelerator and a sliding plate. When the material with a certain downward speed passes through the surface of the sliding plate, it will collide, which can partially clean up the impurities adhered to the surface of the material; On each accelerator, a certain number of pores are opened (the shape of pores can be rectangle, square, circle, ellipse, triangle, diamond, and other special shapes). The airflow blown out from these pores gives the material a driving force in the process of sliding down, which makes the material run down at a faster speed and provides enough momentum for the next impact. Experiments show that for most material, the movement speed is in the range of 0.2 m/s to 50 m/s, which can obtain ideal impact friction effect. Outside this speed range, if it is too low, the separation effect is not ideal, and the residual impurities may not be separated. If it is too high, the material may be broken.

At the lower part of the first-stage accelerated separation unit, there is an arc-shaped back cover. As the arc-shaped back cover is adopted, the upward flow of air in the bottom space is smoother, and at the same time, the arc-shaped back cover makes the space at the lower part of the equipment larger, creating favorable conditions for gravity removal separation unit and third-stage fluidized billowing separation unit.

At the bottom of the accelerator at the bottom of the first-level accelerated separation unit, the movement speed of the material reaches the maximum value. By arranging some strong magnetic units here, the electromagnetic force between the material and impurities can be eliminated to the maximum extent. The acceleration function of the first-stage accelerated separation unit is realized by the multi-stage accelerator and multi-stage sliding plate (or single stage). The angle between the sliding plate and the vertical direction should be less than 80 degrees, while the angle between the accelerator and the horizontal direction is 10~170 degrees (or −80~80 degrees with the vertical direction).

The Third Blanking Station, the Second Gravity Removal Separation Unit

Referring to FIG. 1B, the secondary gravity removal separation unit is a three-dimensional area between the primary accelerated separation unit and the flank mechanism, and the bottleneck between the upper and lower cavities of the equipment is also at this level. When the lower airflow reaches the upper space through this bottleneck, Due to the sudden increase of space, the airflow speed through the bottleneck rapidly increases (not enough to take away the material). The gas in the lower space flows to the secondary gravity removal unit as if it were pumped by a powerful pump, while the gas in the upper space flows to the gas outlet of the equipment as if it were driven by a powerful force with impurities.

Secondary gravity removal separation unit is the main area where impurities are separated from materials. When the materials still carrying impurities from the primary accelerated separation unit pass through it, the impurities will be taken away by the high-speed airflow here. At the same time, the strong magnetic unit on the first-stage accelerated separation unit and the strong magnetic unit on the flank mechanism provide a strong magnetic field here, so this is also the main place for removing electromagnetic force. When the flying material collides with the flank mechanism, the residual impurities attached to the surface of the material will be separated from the material under the collision friction, and this part of the separated impurities will be taken away by the high-speed airflow and flow to the gas outlet.
The Fourth Blanking Station, Three-Stage Fluidized Billowing Separation Unit The three-stage fluidized billowing separation unit of the invention includes a fluidization plate and a three-dimensional space of the upper part thereof, wherein the fluidization plate is provided with a dry air outlet, and the surface of the fluidization plate is mirror-polished, and at the same time, the surface of the fluidization plate is provided with a plurality of small holes, and a part of the gas coming in from the gas inlet enters the lower space through the small holes, and one function of the fluidization plate is to take away the residual impurities on the surface of the material; The fluidization plate is provided with a conductive layer and sufficiently grounded to discharge the static electricity of the material again;

The three-stage fluidized billowing separation unit refers to the three-dimensional space of the fluidization plate and its upper part. In this unit, the material is subjected to the third gas washing separation by the mechanism of fully billowing gas washing, friction and collision, magnetic field eliminating the electromagnetic force of moving material, etc. Once again, the adhesive impurities are eliminated by electromagnetic force, Van der Waals force, liquid bridge and other gravitational forces, and once again, the adhesive impurities are transformed into dispersed impurities, and the dispersed impurities remaining after the previous unit is not separated are separated. And the static electricity of the material is discharged again by means of the conductivity and sufficient grounding of the fluidization plate. Make the cleanliness of the material go up to a higher level, and the impurity content of the material can be reduced to 15 ppm after the cleaner treatment with optimized parameters.

A three-stage fluidized billowing separation unit, which blows the material from the air outlet under the fluidization plate when it comes out of the two-stage gravity removal separation unit and enters the unit. The upper part of the component receives the material from the gravity removal separation unit, and the lower part is connected with a clean outlet; The surface of this component is polished by mirror, in order to avoid the dust generated by friction when the material flows over it. At the same time, the surface is also provided with a number of small holes, through which part of the gas coming in from the gas inlet enters the lower space. One function is to take away the residual impurities on the surface of the material, and the other is to create conditions for the formation of the upper gravity removal separation unit.

The Fifth Blanking Station, the Spectrum Emitter

If the material gets wet or absorbs moisture or suffers from other reasons, it may breed some bacteria or mold, resulting in deterioration and failure of the material. In this patent, a single point or multiple points are internally provided with illumination equipment, and the illumination equipment emits light with a wavelength of 240~280 nm. The light with this wavelength can kill and destroy the molecular structure of DNA (deoxyribonucleic acid) or RNA (ribonucleic acid) in bacteria and viruses, so as to achieve the effect of sterilization and disinfection, and at the same time, it plays an auxiliary role in eliminating the attraction between material and impurities attached to it.

The shape of cleaner and the shape of sliding plate, accelerator, flank mechanism and fluidization plate are not limited to square, but also can be round, semicircular, annular, rectangular, triangular, rhombic, oval and other special shapes. One of the important functions of distribution unit, sliding plate, flank mechanism and fluidization plate is to lead out static electricity of material and impurities. The contact resistance between these facilities and cleaner grounding point should be less than 10 ohms. In non-explosive dangerous places, an ion wind generator can also be installed to enhance the electrostatic removal effect.

Accelerator and sliding plate can be integrated or independent.

Cleaner can operate in either open loop mode or closed loop mode. See the notes for details.

Figure 1M:
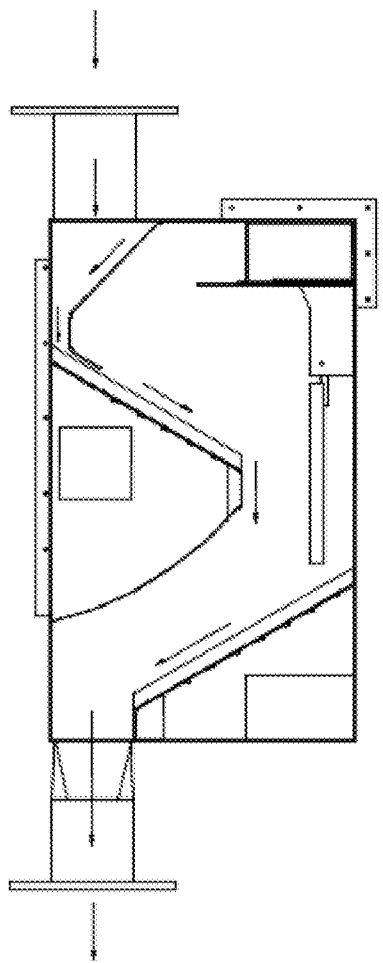

As shown in FIG. 1M, on the basis of the first embodiment, the internal structure of the cleaner can also adopt a one-sided structure for the small-flow (flow less than 20 tons/hour) cleaner, that is, the Material inlet distribution unit, the first-stage accelerated separation unit, the second-stage gravity removal separation unit and the third-stage fluidized bed billowing unit can also adopt a one-sided blanking form. If the space is not limited, even if the flow rate exceeds 20 tons/hour, one-sided blanking can be adopted.

For the working conditions with high cleanliness requirements, the first-class accelerated separation unit, the second-class gravity removal separation unit and the third-class fluidized billowing separation unit can be added. That is, there may be multiple primary accelerated separation unit, multiple secondary gravity removal separation unit, multiple tertiary fluidized billowing separation unit, and expansion of other units.

Internally, the cleaner with small flow (flow less than 20 t/h) can also adopt one-sided structure, that is, the Material inlet distribution unit, the first-stage accelerated separation unit, the second-stage gravity removal separation unit and the third-stage fluidized billowing separation unit can also adopt one-sided blanking. If the space is not limited, even if the flow rate exceeds 20 tons/hour, one-sided blanking can be adopted.

For the working conditions with high cleanliness requirements, the first-class accelerated separation unit, the second-class gravity removal separation unit and the third-class fluidized billowing separation unit can be added. That is, there may be multiple primary accelerated separation unit, multiple secondary gravity removal separation unit, multiple tertiary fluidized billowing separation unit, and expansion of other units.

Accelerator and sliding plate can be integrated or independent.

Example 5

The application of method of accelerating material cleaning with strong magnet particles is characterized in that it is applied to a material purification system to obtain a strong magnet particle accelerating material purification system.

The composition of strong magnet particle accelerated material purification system can be open-loop or closed-loop. Open loop, the wind with impurities coming out of the gas outlet of the strong magnet particle acceleration material cleaner is directly discharged after being treated and is not reused; Closed loop, otherwise, the treated wind will be sent to the gas inlet of the strong magnet particle acceleration material cleaner for repeated use. Open loop, high energy consumption, many equipments, no dangerous gas accumulation and high safety; Closed loop, less energy consumption, less equipment and poor safety due to explosive gas accumulation.

Figure 2B:
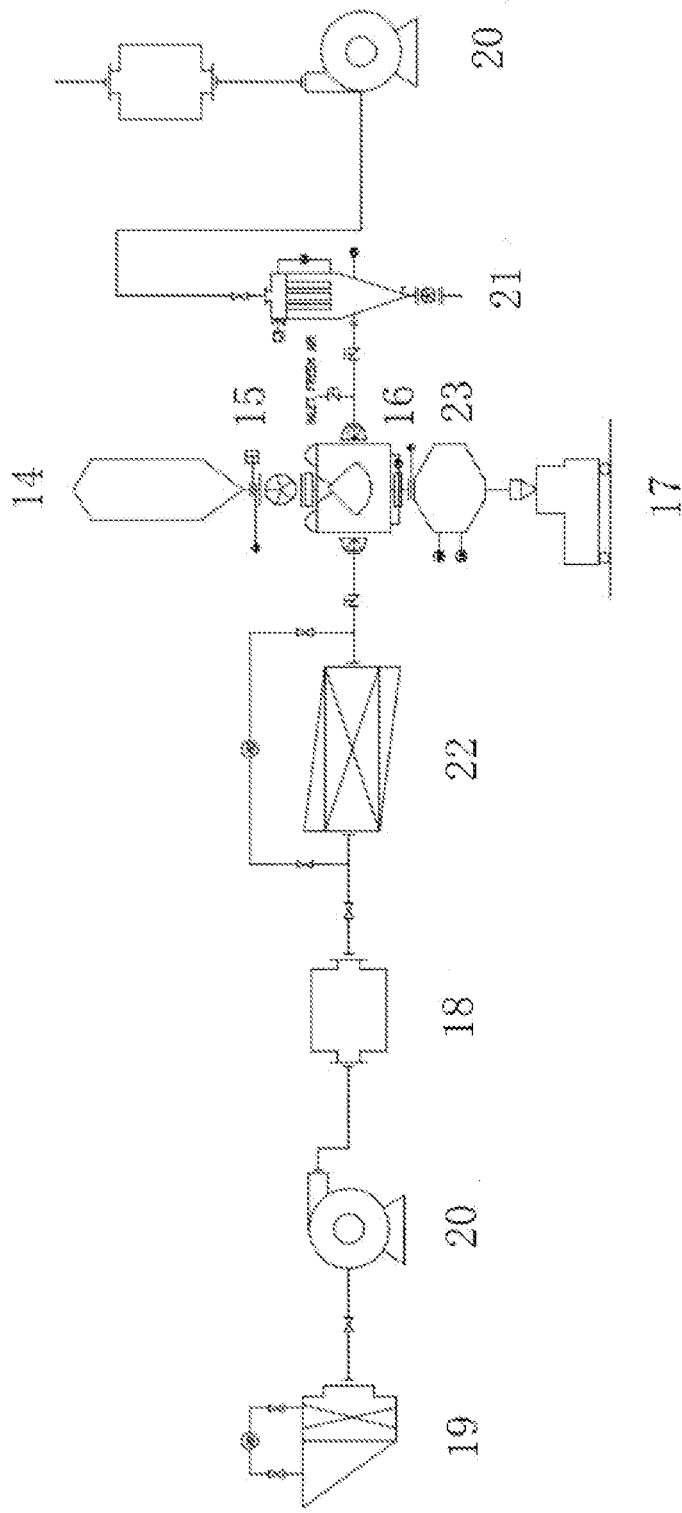

As shown in FIG. 2B, the open-loop system. The cleaner of the second embodiment can form a material purification system with valve such as fan, filter, cyclone, rotary valve or slide valve, silencer, isolation hopper (optional), etc. It means that the gas inlet and gas outlet of the material purification system are both open. Generally, the system is equipped with two fans, which are located in the gas outlet and gas inlet respectively, and their outlets and inlets are directly connected with the gas outside the system.

Figure 2C:
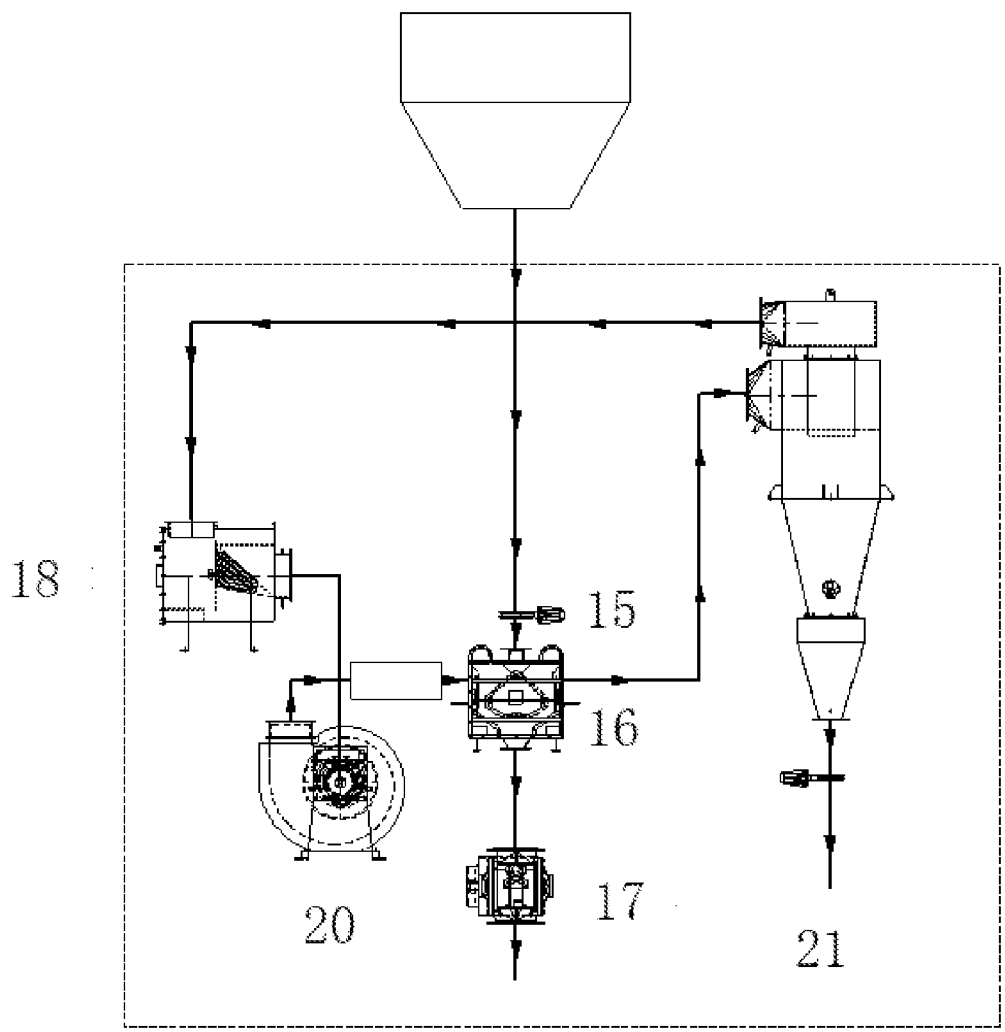

As shown in FIG. 2C, the closed-loop system. The cleaner of the second embodiment can form a material purification system with valve such as fan, filter, cyclone, rotary valve or slide valve, silencer, isolation hopper (optional), etc. It means that the process of the purified gas system of this material is closed, and a fan provides gas power, with cleaner as the core, and air purification equipment on both sides of it as the auxiliary. The purified gas is recycled repeatedly, and each cycle must be purified by purification facilities.

Note ①  Material: The material referred to in this patent document refers to a non-metallic solid material with a certain particle size, and its shape can be spherical, oblong, square, cylindrical, drop-shaped, and other irregular shapes with a size of 0.5~20 mm Note ②: Impurities: Impurities referred to in this patent refer to dust, fluff, ribbons, debris, water droplets, flakes, fragments, dust, liquid droplets, etc. mixed in material.

Dust, dust and debris in impurities generally refer to particles with a particle size of less than 500 μm. The impurities can be the same as or different from the material, and can be particles, dust, ribbons or fluff. Impurities can be solid, liquid or liquid droplets.

Note ③: Closed-loop system: it means that the process of the purified gas system of this material is closed, with a fan providing gas power, with cleaner as the core, and air purification equipment on both sides of it as assistance. The purified gas is recycled repeatedly, and each cycle must be purified by purification facilities.

Note ④ Closed-loop system: it means that the process of the purified gas system of this material is closed, and a fan provides gas power, with cleaner as the core, and air purification equipment on both sides of it as the auxiliary. The purified gas is recycled repeatedly, and each cycle must be purified by purification facilities.

Note ⑤: Electromagnetic force: The electrostatic attraction and magnetic field attraction between material and impurities are collectively referred to as electromagnetic force.

Note ⑥ One-sided blanking: One-sided blanking is relative to two-sided blanking. Refer to FIG. 1M for the schematic diagram of one-sided blanking.

What is claimed is:

1. A method of accelerating particles material cleaning with a strong magnet, comprising:
   a material enters from a material inlet; an acceleration of the material is achieved by a wind airflow with an accelerator, wherein material particles move with a predetermined speed, and a location point and a speed when the material reaches a maximum speed is configured to be controlled, wherein a material speed is regulated by a wind speed, and the location point when the material reaches the maximum speed is a speed of an end area of the accelerator;
   a strong magnetic field unit is installed at a point where the material enters from the material inlet and exits from a material exit; wherein the strong magnetic field unit is installed adjacent to the point where the material reaches the maximum speed; the internal strong magnetic field unit is configured to generate an internal strong magnetic field;
   the internal strong magnetic field eliminates an electromagnetic force, a van der Waals force, and a liquid bridge between the material and the impurities attached to a material surface; at the same time, combined with the wind airflow and a frictional collision with internal parts, the van der Waals force and the liquid bridge between the material particles and the impurities attached to the material particles are weakened, improving a cleanliness of the material.

2. The method according to claim 1, wherein the strong magnetic field is generated by strong permanent magnet materials or electromagnetic coils, wherein the strong permanent magnet materials or the electromagnetic coils are distributed at one point or multiple places, and a magnetic induction intensity is higher than 600 gauss, wherein the magnetic induction intensity is distributed adjacent to an area with a high material flowing speed and located at an installation point within 2 mm of a strong magnet; the strong magnetic field unit is integrated, attached and matched with other units in a physical space, and together with the moving particles and the impurities, an electrostatic and a remanence existing between the particles and the impurities attached to surfaces of the particles is configured to generate an electromagnetic force in opposite directions, wherein the particles and the impurities are configured to generate gaps or separate, and the attached impurities are configured to be converted into dispersed impurities to improve a cleaning effect; the volume, a size and shape of the strong magnet match working conditions, wherein the strong magnet constitutes the strong magnetic field unit; a generation of the strong magnetic field of the strong magnetic field unit is also configured to be realized by connecting DC, AC and various harmonic power supplies to the electromagnetic coil; besides using DC, wherein an electromagnetic radiation intensity is less than a relevant standards.

3. The method according to claim 1, wherein the wind airflow comprises at least a two-stage separation, comprising at least one permutation and combination of an accelerated separation, a gravitational separation and a fluidized billowing separation.

4. The method according to claim 3, wherein the accelerated separation comprises the following steps: the internal strong magnetic field unit and an accelerated separation unit are configured to realize the accelerated separation, and the acceleration of the material depends on an airflow sprayed by the accelerator in the accelerated separation unit to act on the material particles to accelerate the material particles step by step or single stage, resulting in a rapid movement;
   at an end of the accelerated separation unit, a particle speed is accelerated or adjusted to more than 0.2 m/s; when the particle speed increases, a purification effect is improved, but an excessive speed will damage the particles; wherein the particle speed is set at an upper limit, wherein the upper limit is generally lower than 50 m/s and depends on a nature of a specific material.

5. The method according to claim 3, wherein the gravitational separation comprises the following processes: when the material still carrying impurities passes through at least the two-stage separation comprising the at least one permutation and combination of the accelerated separation, the gravitational separation and the fluidized billowing separation, the impurities will be taken away by the high-speed airflow; at the same time, the strong magnetic field unit on a flank mechanism provides a strong magnetic field here, so the strong magnetic field unit is further a main place to remove the electromagnetic force;
   a gravity removal separation unit comprises the conductive and grounded flank mechanism and the strong magnetic field unit arranged on the flank mechanism; under an action of the internal strong magnetic field unit and the conductive and grounded flank mechanism, an attraction and a static electricity on the material are eliminated; when the flying material hits and rubs the flank mechanism, residual impurities attached to the material surface will be separated from the material under a collision friction, and the part of separated impurities will be taken away by the high-speed airflow and flow to a gas outlet.

6. The method according to claim 3, wherein the fluidized billowing separation comprises the following processes: a fluidization unit is configured to fluidize the material, an attraction between granular materials and impurities attached to a surface of the granular materials is eliminated again, and a pure gas is configured to fully wash, separate and purify the material to enhance a separation effect of the material and impurities.

7. The method according to claim 6, wherein the fluidized billowing separation is realized by adjusting a size of a fluidization plate hole in the fluidization unit from 0.5 mm-5 mm to 5 mm and an opening of an air valve.

8. The method according to claim 1, wherein if the material is wet or absorbs moisture or is subjected to other reasons, some bacteria or molds may breed, resulting in a deterioration and failure of the material, at least one selected from the group consisting of a spectrum generator, a microwave generator and a plasma generator is configured for an auxiliary gravity elimination and sterilization of the material, cleaner internals, gases and the impurities; a wavelength of spectrum emitted by the spectrum generator is 250~280 nm, and an illumination intensity of the spectrum generator is controlled above 18 $\mu W/cm^2$.

9. A device using a method of accelerating particles material cleaning with a strong magnet, wherein by applying the method to a material cleaner to obtain the device, the device is a strong magnet particle acceleration material cleaner; the strong magnet particle acceleration material cleaner comprises a case, and the case comprises:

a blanking separation unit, wherein the blanking separation unit is equipped with material acceleration component and comprises an accelerator, a gas inlet and a gas outlet; the blanking separation unit comprises at least two stages of separation, comprising at least one permutation combination of an accelerated separation unit, a gravity removal separation unit and a fluidized billowing separation unit;

a strong magnetic field unit is arranged inside where a material enters from a material inlet and exits from a material exit;

the material enters from the material inlet, and a wind airflow cooperates with the accelerator to realize an acceleration of the material, wherein material particles move at a predetermined speed, and a position point when the material reaches a highest speed is a speed at an end of the accelerator;

an internal strong magnetic field is generated by using the internal strong magnetic field unit, wherein the internal strong magnetic field is configured to eliminate attractive forces comprising an electromagnetic force, a van der Waals force and a liquid bridge between the material and impurities attached to a surface of the material; at the same time, the internal strong magnetic field is configured to cooperate with the wind airflow, weaken the van der Waals force between the material particles and the impurities attached to the material particles by a friction and a collision with internal parts, and improve a cleanliness of the material.

10. The device according to claim 9, wherein the strong magnetic field unit comprises a strong permanent magnet or an electromagnetic coil distributed at one point or multiple places, and is located in an area where the material flows, wherein the area comprises the material inlet of equipment, the material exit of equipment, and the accelerated separation unit; on the gravity removal separation unit and the fluidized billowing separation unit, the permanent magnets are distributed as adjacent as possible to the area where the material flows at a high speed, and a magnetic induction intensity at 2 mm of an installation point of a strong magnet is higher than 600 gauss; wherein the strong magnetic field unit is arranged adjacent to the position point when the material reaches the highest speed;

a volume, size and shape of the strong magnet match working conditions, wherein the strong magnet constitutes the strong magnetic field unit; a generation of the strong magnetic field of the strong magnetic field unit is configured to be realized by connecting DC, AC and various harmonic power supplies to the electromagnetic coil; besides using DC, an electromagnetic radiation intensity is less than relevant standards.

11. The device according to claim 9, wherein a one-sided blanking separation unit, a two-sided blanking separation unit or multiple groups of blanking separation units are arranged in the case; for working conditions with high requirements for the cleanliness, a combination of multiple accelerated separation units, multiple gravity removal separation units, multiple fluidized billowing separation units, and an expansion of other units are adopted in a single-side blanking assembly.

12. The device according to claim 9, wherein the accelerated separation unit are provided with 1-stage or multi-stage accelerators, 1-stage or multi-stage sliding plates and wind distribution ports, a comprised angle between the 1-stage or multi-stage sliding plates and a vertical direction is less than 80 degrees, and a comprised angle between the 1-stage or multi-stage accelerator and a horizontal direction is 10-170 degrees or a comprised angle between the 1-stage or multi-stage accelerator and the vertical direction is −80-80 degrees; each 1-stage or multi-stage accelerator is provided with a predetermined number of pores, wherein the predetermined number of pores are matched with the wind distribution port to make an airflow ejected from the 1-stage or multi-stage accelerator act on the material, accelerate a movement speed of the material particles, and at the same time make the dispersed impurities separate from the material flow; the 1-stage or multi-stage accelerator and the 1-stage or multi-stage sliding plate are configured to be integrated or independent of each other.

13. The device according to claim 9, wherein the gravity removal separation unit comprises a flank mechanism, the flank mechanism comprises side flaps, a manual adjustment machinery, and a wind distribution mechanism.

14. The device according to claim 9, wherein the fluidized billowing separation unit comprises a fluidization plate and a three-dimensional space, wherein a upper part of the fluidization plate belongs to the three-dimensional space; the fluidization plate is provided with a dry air outlet, wherein a part of a gas coming in from the gas inlet enters a lower space through the dry air outlet; a first function is to make the material billow, turn over, collide, wash away residual impurities, and a second function is to provide a required gas for an upper stage; the fluidization plate is provided with a conductive layer and sufficiently grounded to discharge a static electricity of the material again; a size of fluidization plate holes in the fluidized billowing separation unit is 0.5 mm-5 mm.

15. The device according to claim 9, wherein at least one group of a spectrum generator, a microwave generator or a plasma generator is set at at least one point in the case, wherein the at least one group of the spectrum generator, the microwave generator or the plasma generator is configured for an auxiliary gravity elimination and sterilization of the material, cleaner internals, gases and the impurities; the wavelength of spectrum emitted by the spectrum generator is 250~280 nm, and an illumination intensity of the spectrum generator is controlled above 18 μW/cm².

16. The device according to claim 9, wherein a shape of the case of the strong magnet particle acceleration material cleaner and shapes of a sliding plate, an accelerator, a flank mechanism and a fluidization plate are not limited to a square, and are configured to be round, semicircular, annular, rectangular, triangular, diamond, and oval.

17. The device according to claim 9, wherein one of important functions of a distribution unit, a sliding plate, a flank mechanism and a fluidization plate is to lead out a static electricity of materials and impurities; a contact resistance between the distribution unit, the sliding plate, the flank mechanism and the fluidization plate and a cleaner grounding point is less than 10 ohms, and an ion wind generator is configured to be optionally installed in non-explosive dangerous places to enhance an effect of removing the static electricity of materials.

18. A device using the method of accelerating particles material cleaning with a strong magnet according to claim 1, wherein by applying the method to a material purification system to obtain the device, the device is a strong magnet particle accelerating material purification system.

19. The device according to claim 10, wherein a one-sided blanking separation unit, a two-sided blanking separation unit or multiple groups of blanking separation units are arranged in the case; for working conditions with high requirements for the cleanliness, a combination of multiple accelerated separation units, multiple gravity removal separation units, multiple fluidized billowing separation units, and an expansion of other units are adopted in a single-side blanking assembly.

20. The device according to claim 11, wherein one of important functions of a distribution unit, a sliding plate, a flank mechanism and a fluidization plate is to lead out a static electricity of materials and impurities; a contact resistance between the distribution unit, the sliding plate, the flank mechanism and the fluidization plate and a cleaner grounding point is less than 10 ohms, and an ion wind generator is configured to be optionally installed in non-explosive dangerous places to enhance an effect of removing the static electricity of materials.

* * * * *